United States Patent
Fitzgerald et al.

(10) Patent No.: US 10,112,056 B2
(45) Date of Patent: Oct. 30, 2018

(54) OPTIMISING CURRENT DIRECTION AND INTENSITY OF TRANSCRANIAL MAGNETIC STIMULATION

(71) Applicant: Monash University, Clayton (AU)

(72) Inventors: Paul B. Fitzgerald, Hampton (AU); Richard H. Thomson, Hobart (AU)

(73) Assignee: Monash University (AU)

( * ) Notice: Subject to any disclaimer, the term of this patent is extended or adjusted under 35 U.S.C. 154(b) by 489 days.

(21) Appl. No.: 14/402,925

(22) PCT Filed: May 22, 2013

(86) PCT No.: PCT/AU2013/000540
§ 371 (c)(1),
(2) Date: Nov. 21, 2014

(87) PCT Pub. No.: WO2013/173875
PCT Pub. Date: Nov. 28, 2013

(65) Prior Publication Data
US 2015/0174423 A1 Jun. 25, 2015

(30) Foreign Application Priority Data
May 25, 2012 (AU) ................................ 2012902163

(51) Int. Cl.
*A61N 2/12* (2006.01)
*A61N 2/02* (2006.01)
(Continued)

(52) U.S. Cl.
CPC .............. *A61N 2/02* (2013.01); *A61B 5/0075* (2013.01); *A61B 5/026* (2013.01); *A61B 5/0484* (2013.01);
(Continued)

(58) Field of Classification Search
CPC ........ A61B 5/14542; A61B 5/14551–5/14557; A61N 2/00–2/12
See application file for complete search history.

(56) References Cited

U.S. PATENT DOCUMENTS

2005/0107654 A1    5/2005   Riehl
2007/0282189 A1    12/2007   Dan et al.
(Continued)

FOREIGN PATENT DOCUMENTS

CN    201453834 U    5/2010
CN    102302823 A    1/2012
(Continued)

OTHER PUBLICATIONS

English translation of JP 2009022660.*
(Continued)

*Primary Examiner* — Thaddeus Cox
(74) *Attorney, Agent, or Firm* — Lerner, David, Littenberg, Krumholz & Mentlik, LLP (57) ABSTRACT

A method of optimizing transcranial magnetic stimulation is described. An electrical signal is applied to a coil to generate one or more magnetic field pulses for transcranial magnetic stimulation of a target cortical region of a patient. The transcranial magnetic stimulation has stimulation parameters including orientation of the coil relative to the patient and intensity of the magnetic stimulation. At least the orientation of the coil relative to the patient is varied. At different orientations of the coil relative to the patient, neuron activation at the target cortical region is determined by monitoring changes in blood flow and/or blood oxygenation, e.g. using near infra-red spectroscopy. Based on information obtained during the monitoring, one or more
(Continued)

optimal coil orientations for the transcranial magnetic stimulation are determined. Apparatus for carrying out the method is also described.

10 Claims, 8 Drawing Sheets

(51) Int. Cl.
    *A61B 5/00* (2006.01)
    *A61B 5/026* (2006.01)
    *A61B 5/0484* (2006.01)
    *A61B 5/0488* (2006.01)
    *A61B 5/055* (2006.01)
    *A61B 5/145* (2006.01)
    *A61N 2/00* (2006.01)
(52) U.S. Cl.
    CPC ............ *A61B 5/0488* (2013.01); *A61B 5/055* (2013.01); *A61B 5/14542* (2013.01); *A61N 2/006* (2013.01)

(56) References Cited

U.S. PATENT DOCUMENTS

| | | |
|---|---|---|
| 2009/0227830 A1 | 9/2009 | Pillutla et al. |
| 2011/0118534 A1 | 5/2011 | Baror et al. |
| 2011/0288364 A1 | 11/2011 | Zangen et al. |
| 2012/0165696 A1 | 6/2012 | Arns |

FOREIGN PATENT DOCUMENTS

| | | | |
|---|---|---|---|
| JP | 2009022660 A | * | 2/2009 |
| WO | 2003098268 A1 | | 11/2003 |
| WO | 2010049575 A1 | | 5/2010 |

OTHER PUBLICATIONS

Richter et al., "Optimal Coil Orientation for Transcranial Magnetic Stimulation," PLOS One, vol. 8 Issue 4, Apr. 2013, p. 1-10.*

Thomson et al., "Blood oxygenation changes resulting from suprathreshold transcranial magnetic stimulation", PubMed, Jul. 2011, 4(3):165-168.

Kähkönen et al., "Prefrontal TMS produces smaller EEG responses than motor-cortex TMS: implications for rTMS treatment in depression", PubMed, Psychopharmacology, Aug. 2005; 11(1):16-20.

Köhkönen et al., "Distinct differences in cortical reactivity of motor and prefrontal cortices to magnetic stimultation", PubMed, Clin Neutophysiol., Mar. 2004; 115(3):583-588.

Bonato et al., "Transcranial magnetic stimulation and cortical evoked potentials: a TMS/EEG co-registration study", PubMed, Clin Neurophysiol., Aug. 2006; 117(8):1699-707.

Balslev, D. et al., 'Inter-individual variability in optimal current direction for transcranial magnetic stimulation of the motor cortex', Journal of Neuroscience Methods, 2007, vol. 162, pp. 309-313 Abstract; p. 310, colunm1, lines 24-30.

Brasil-Neto, J.P. et al., 'Optimal Focal Transcranial Magnetic Activation of the Human Motor Cortex: Effects of Coil Orientation, Shape of the Induced Current Pulse, and Stimulus Intensity', Journal ofClinicaJ Neurophysiology, 1992, vol. 9, No. 1, pp. 132-136 Abstract; Fig. 2; p. 133, col. 2, Lines 4-5, 16-32; p. 134, col. 4, Line 1-col. 5, line 6.

Dubach, P. et al., 'Significance of coil orientation for motor evoked potentials from nasalis muscle elicited by transcranial magnetic stimulation', ClinicaJ Neurophysiology, 2004, vol. 115, pp. 862-870 Abstract; p. 863, col. 1, lines 14-47; p. 864, col. 1, line 35-col. 2, line 30.

Fantini, S. et al., "Non-invasive optical monitoring of the newborn piglet brain using continuous-wave and frequency-domain spectroscopy", Physics in medicine and biology 44, 1543-1563 (1999).

International Search Report and Written Opinion for Application No. PCT/AU2013/000540 dated Jul. 22, 2013.

Niyazov, D.M. et al., 'Functional magnetic resonance imaging and transcranial magnetic stimulation: Effects of motor imagery, movement and coil orientation', Clinical Neurophysiology, 2005, vol. 116, pp. 1601-1610, p. 1601, col. 2, line 9-p. 1602, col. 1, line 5.

Toronov, V. et al., "Investigation of human brain hemodynamics by simultaneous near-infrared spectroscopy and functional magnetic resonance imaging", Medical physics 28, 521-527 (2001).

Extended European Search Report for EP13794782.6 dated Mar. 15, 2016.

* cited by examiner

OPTIMISING CURRENT DIRECTION AND INTENSITY OF TRANSCRANIAL MAGNETIC STIMULATION

CROSS-REFERENCE TO RELATED APPLICATION

The present application is a national phase entry under 35 U.S.C. § 371 of International Patent Application No. PCT/AU2013/000540, filed May 22, 2013, published in English as WO 2013/173875 A1, which claims the priority from Australian Provisional Patent Application No 2012902163 filed on 25 May 2012, the contents of which are incorporated herein by reference.

TECHNICAL FIELD

The present disclosure relates to transcranial magnetic stimulation and particularly, although not necessarily exclusively, methods and devices for determining optimal transcranial magnetic stimulation current direction and intensity at the cortex.

BACKGROUND

Since its conception, transcranial magnetic stimulation (TMS) has become an important tool in neurophysiology and biological psychiatry. The application of repetitive stimulation has been shown to produce changes in brain activity and it is increasingly being applied in therapeutic applications such as major depressive disorder, schizophrenia and autism.

TMS may be applied to various regions of the brain including the motor cortex, and the prefrontal cortex. Commonly, TMS is applied non-invasively using a coil, such as a 'figure-of-8' coil, which is positioned externally to the patient and held adjacent the target cortical region. A large transient current is delivered to the coil, generating one or more magnetic pulses that induce ionic current flow in the cortex that can depolarize (activate) neurons.

In addition to the intensity of the magnetic stimulation, the degree of elicited neuron activity is affected by the coil orientation relative to the scalp. This is a direct result of neurons being preferentially stimulated by ionic current travelling in a particular direction, the direction of ionic current flow being altered by altering the coil orientation. The optimal orientation for stimulating the motor cortex, for example, is typically 45° to a parasagittal plane of the patient.

To ensure that desired therapeutic outcomes can be realised, it is important to determine a threshold at which the TMS provides neuron depolarization and thus a therapeutically relevant change in neuron activity. In the case of TMS applied to the motor cortex, for example, a stimulation intensity required to activate a certain muscle, e.g., a thumb, is known as the resting motor threshold (rMT).

However, therapeutic treatments using TMS typically target cortical brain regions that are outside of the motor cortex such as the prefrontal cortex (PFC), in which regions TMS elicits no readily observable indication that a threshold stimulation level has been reached. Overall, there has been no straightforward method for determining the threshold stimulation level or optimal coil orientation (appropriate "TMS parameters") at the PFC or other brain regions outside of the motor cortex at which neuron depolarization takes place.

Traditionally, it has been assumed the TMS parameters that are appropriate for the motor cortex will also be appropriate at the other target cortical regions. However, this is not necessarily the case due to differences in the scalp to cortex distance at different regions of the scalp and other factors such as variation in direction of nerve fibres. The assumption may therefore lead to reduced TMS treatment efficacy for certain patients. It follows that, by determining TMS parameters specific to a target cortical region, treatment efficacy can be improved.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to one aspect, there is provided a transcranial magnetic stimulation method comprising:
applying an electrical signal to a coil to generate one or more magnetic field pulses for transcranial magnetic stimulation of a target cortical region of a patient;
varying the orientation of the coil relative to the patient; and
at different orientations of the coil relative to the patient, monitoring neuron activation at the target cortical region using near infra-red spectroscopy.

By monitoring neuron activation at the target cortical region using near infra-red spectroscopy at different coil orientations, one or more optimal coil orientations for transcranial magnetic stimulation (TMS) of the target cortical region can be determined.

Thus, according to one aspect, there is provided a method of optimising transcranial magnetic stimulation, the method comprising:
applying an electrical signal to a coil to generate one or more magnetic field pulses for transcranial magnetic stimulation of a target cortical region of a patient;
varying the orientation of the coil relative to the patient;
at different orientations of the coil relative to the patient, monitoring neuron activation at the target cortical region using near infra-red spectroscopy; and
based on information obtained during the monitoring, determining one or more optimal coil orientations for the transcranial magnetic stimulation.

The methods discussed above may further comprise varying parameters of the electrical signal applied to the coil and, for different parameters of the electrical signal, monitoring neuron activation at the target cortical region. Again, monitoring of the neuron activation may use near infra-red spectroscopy. Parameters of the electrical signal to be varied may include the current level, pulse frequency and/or pulse width, which are parameters that can affect the intensity of the TMS applied to the target cortical region. By monitoring neuron activation at the target cortical region for different parameters of the electrical signal, minimum (threshold) intensity for TMS can be determined.

According to another aspect, there is provided transcranial magnetic stimulation apparatus comprising:
a coil;
an electrical signal generator for delivering an electrical signal to the coil, wherein upon delivery of the electrical signal to the coil, the coil generates one or more magnetic field pulses for transcranial magnetic stimulation of a target cortical region of a patient;

means for varying the orientation of the coil relative to the patient; and a monitoring device configured to use near infra-red spectroscopy to monitor neuron activation at the target cortical region at different orientations of the coil relative to the patient.

By using the monitoring device to monitor neuron activation at the target cortical region using near infra-red spectroscopy at different coil orientations, one or more optimal coil orientations for transcranial magnetic stimulation (TMS) of the target cortical region can be determined.

According to yet another aspect, there is provided transcranial magnetic stimulation apparatus adapted to optimise transcranial magnetic stimulation, the apparatus comprising:

a coil;

an electrical signal generator for delivering an electrical signal to the coil, wherein upon delivery of the electrical signal to the coil, the coil generates one or more magnetic field pulses for transcranial magnetic stimulation of a target cortical region of a patient;

means for varying the orientation of the coil relative to the patient;

a monitoring device configured to use near infra-red spectroscopy to monitor neuron activation at the target cortical region at different orientations of the coil relative to the patient; and an analysis unit configured to receive information about the neuron activation obtained during the monitoring and, based on the received information, determine one or more optimal coil orientations for transcranial magnetic stimulation of the target cortical region of the patient.

The electrical signal generator in the apparatuses discussed above may be adapted to vary parameters of the electrical signal applied to the coil. The monitoring device may be configured to monitor neuron activation at the target cortical region at different parameters of the electrical signal. Again, monitoring of the neuron activation may use near infra-red spectroscopy and parameters of the electrical signal to be varied may include the current level, pulse frequency and/or pulse width, which parameters can affect the intensity of the TMS applied to the target cortical region. By using the monitoring device to monitor neuron activation at the target cortical region for different parameters of the electrical signal, minimum (threshold) intensity for TMS can be determined. In one embodiment, the processor that receives information about the neuron activation obtained during the monitoring may, based on the received information, determine threshold intensity for TMS of the target cortical region of the patient.

Near infra-red spectroscopy (NIRS) is a technique that can be used to measure changes in blood oxygenation (HbO) levels in cortical regions of the brain non-invasively; HbO changes are associated with changes in oxygen uptake by neurons activated by transcranial magnetic stimulation (TMS). The inventors have determined that, as for varying the stimulation intensity, varying the coil orientation relative to the patient produces differential changes in HbO. When a 'figure-of-8' coil is used, which has two substantially identical loops ('wings') joined together at respective sides, varying the orientation of the coil can include varying the angle of a central axis, which lies along a line of symmetry between the two loops, relative to a parasagittal plane of the patient. While varying the angle, the centre of the coil may be maintained on the parasagittal plane.

The method and apparatus disclosed herein is considered particularly appropriate for determining suitable TMS parameters for cortical regions outside of the motor cortex, such as the pre-frontal cortex (PFC). As discussed above, there has existed no straightforward method for determining such TMS parameters at the PFC or other brain regions outside of the motor cortex since, for example, there is no readily visible or measurable response (e.g. a motor response such as thumb movement) upon therapeutically relevant neuron activation at these non-motor regions. Nonetheless, the method disclosed herein is not limited to determining one or more TMS parameters for non-motor cortical regions. The skilled person will appreciate that the method may also be used for determining TMS parameters at the motor cortex as an alternative or an adjunct to the monitoring of motor responses or otherwise.

NIRS uses specific wavelengths of near infrared light to noninvasively illuminate cortical brain tissue below a sensor (e.g. a probe) of a monitoring device, which sensor is placed on a patient's scalp. The light scatters in the tissue and is absorbed differently dependent on the amount of oxygen attached to blood/hemoglobin. Light that is not absorbed is returned as an optical signal to the sensor which is converted by the probe or monitoring device into an electrical NIRS signal that is indicative of absorption and scattering coefficients and ultimately can be used to determine a ratio of oxygenated blood to non-oxygenated blood. In embodiments discussed herein, the extent of neuron activation is quantified by monitoring changes in DC, AC and/or phase of a collected NIRS signal or otherwise. This quantification may be used to build patient response profiles for the neuron activation resulting from different TMS parameters. Response profiles may be expressed in the form of graphs, tables, one or more numerical values, and/or otherwise. In some embodiments, NIRS profiles are expressed as graphs of the average change in HbO (a.u.) over time.

NIRS may be used exclusively as a monitoring technique to determine changes in neural activation at the target cortical region in order to determine TMS parameters. However, NIRS may also be used in combination with other monitoring techniques. Electroencephalography (EEG) may be used in combination with NIRS, for example. In one embodiment, EEG electrodes may be located on the scalp of the patient adjacent the target cortical region, e.g. adjacent the NIRS probe. Upon TMS, evoked potentials at the EEG electrodes may be determined for different TMS parameters and an EEG response profile may be generated. The EEG monitoring may be carried out over multiple trial periods and the evoked potentials may be averaged out over these periods in order to separate out phase-locked cortical responses to the TMS stimulation. By using both NIRS and EEG to analyse the neural response, changes to both the brain's circulatory system and electrical field, resulting from changes in neural activity due TMS, can be determined. Overall, this can give a more complete picture of neural response than using only one of these techniques.

EEG profiles may be expressed in the form of graphs, tables, one or more numerical values, and/or otherwise. In one embodiment, EEG profiles are expressed as a graph of the average cortical evoked potential (voltage) evoked at each stimulation level.

By carrying out measurements using NIRS alone, or in combination with another technique such as EEG, an NIRS or an NIRS/EEG patient response profile, etc., for different TMS parameters, including coil orientation, may be determined. Following from this, TMS parameters for a target cortical region of a patient may be calculated as part of a therapeutic protocol.

In determining TMS parameters including coil orientation, the monitoring of changes in neural activity at a target cortical region outside of the motor cortex using NIRS, and optionally also EEG, may be combined with monitoring changes in neural activity at the motor cortex. Monitoring of the motor cortex may be performed simultaneously or before or after monitoring of non-motor target cortical region.

Monitoring of the motor cortex in addition to monitoring the non-motor target cortical region may have a number of advantageous applications. As one example, by generating response profiles, such as NIRS or NIRS/EEG response profiles, for both the motor cortex and the target cortical region, the response profiles can be compared to determine suitable or optimal stimulation parameters. For example, TMS parameters for the target cortical region can be determined on the basis that the parameters elicit a response profile that corresponds to or is closest to a response profile generated for the motor cortex when a motor threshold is achieved. To determine that a motor threshold has been achieved, in addition to visual observation, techniques such as electromyography (EMG) may be employed. The response profiles at the target cortical region and the motor cortex may be determined simultaneously or otherwise.

As indicated, near infra-red spectroscopy (NIRS) is a technique that can be used to measure changes in blood oxygenation (HbO) levels in cortical regions of the brain non-invasively and therefore monitor neuron activation. The inventors have determined that varying the coil orientation relative to the patient produces differential changes in HbO and one way to measure these changes is through NIRS. However, in aspects of the present disclosure it is also recognised that alternative techniques may be taken to measure neuron activity based on a similar proxy of changes in blood flow and blood oxygen that follow metabolic processes. An example alternative technique in this regard is functional magnetic resonance imaging (fMRI), which can use the blood-oxygen-level-dependent (BOLD) contrast to map neural activity. FMRI or another technique may therefore be employed as a direct replacement of, or as an adjunct to, NIRS, in order to monitor neuron activation.

According to one aspect, there is provided a transcranial magnetic stimulation method comprising:

applying an electrical signal to a coil to generate one or more magnetic field pulses for transcranial magnetic stimulation of a target cortical region of a patient;

varying the orientation of the coil relative to the patient; and at different orientations of the coil relative to the patient, monitoring changes in blood flow and/or blood oxygenation at the target cortical region.

According to another aspect, there is provided a method of optimising transcranial magnetic stimulation, the method comprising:

applying an electrical signal to a coil to generate one or more magnetic field pulses for transcranial magnetic stimulation of a target cortical region of a patient;

varying the orientation of the coil relative to the patient;

at different orientations of the coil relative to the patient, monitoring changes in blood flow and/or blood oxygenation at the target cortical region; and based on information obtained during the monitoring, determining one or more optimal coil orientations for the transcranial magnetic stimulation.

According to yet another aspect, there is provided transcranial magnetic stimulation apparatus comprising:

a coil;

an electrical signal generator for delivering an electrical signal to the coil, wherein upon delivery of the electrical signal to the coil, the coil generates one or more magnetic field pulses for transcranial magnetic stimulation of a target cortical region of a patient;

means for varying the orientation of the coil relative to the patient; and a monitoring device configured to monitor changes in blood flow and/or blood oxygenation at the target cortical region at different orientations of the coil relative to the patient.

According to yet another aspect, there is provided transcranial magnetic stimulation apparatus adapted to optimise transcranial magnetic stimulation, the apparatus comprising:

a coil;

an electrical signal generator for delivering an electrical signal to the coil, wherein upon delivery of the electrical signal to the coil, the coil generates one or more magnetic field pulses for transcranial magnetic stimulation of a target cortical region of a patient;

means for varying the orientation of the coil relative to the patient;

a monitoring device configured to monitor changes in blood flow and/or blood oxygenation at the target cortical region at different orientations of the coil relative to the patient; and an analysis unit configured to receive information about the changes in blood flow and/or blood oxygenation obtained during the monitoring and, based on the received information, determine one or more optimal coil orientations for transcranial magnetic stimulation of the target cortical region of the patient.

The changes in blood flow and/or blood oxygenation may be monitored using NIRS, fMRI or other techniques.

Where fMRI is used, for example, fMRI may be used exclusively as a monitoring technique to determine changes in neural activation at the target cortical region in order to determine TMS parameters. However, fMRI may also be used in combination with other monitoring techniques. Electroencephalography (EEG) may be used in combination with fMRI, for example, in a manner similar or identical to that described above with respect to NIRS. By carrying out measurements using fMRI alone, or in combination with other techniques such as EEG, or even NIRS, different optimal TMS parameters, including coil orientation, may be determined as part of a therapeutic protocol.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments are now described with reference to the accompanying drawings, in which.

DESCRIPTION OF EMBODIMENTS

Figure 1:
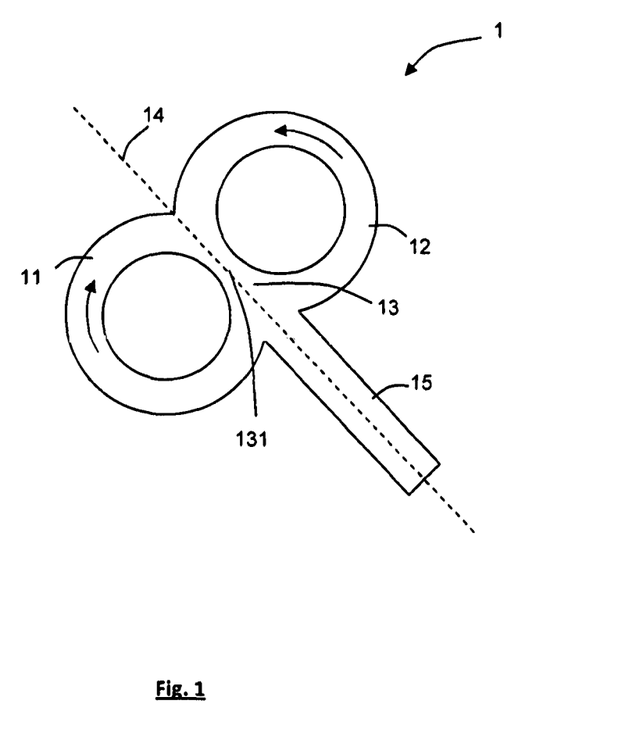
FIG. 1 shows a top view of a 'figure-of-8' coil for use in methods and apparatus according to embodiments of the present disclosure.
Figure 2A:
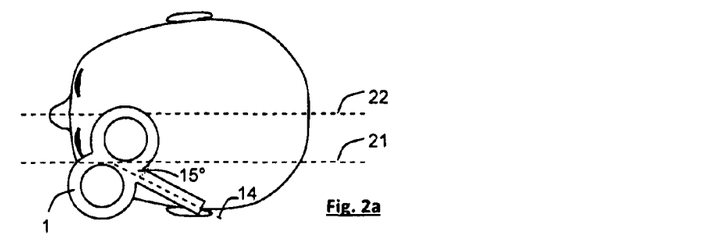
FIGS. 2a to 2e shows a top view of the coil of FIG. 1 positioned at different orientations relative to a patient's scalp.
Figure 2B:
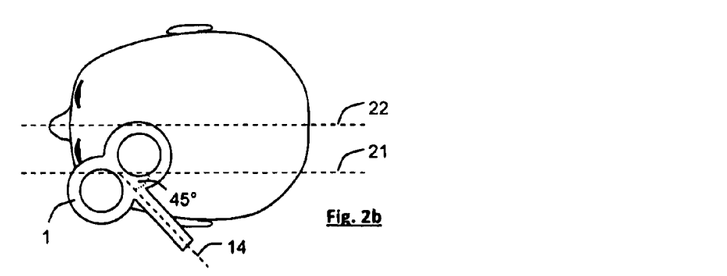
Figure 2C:
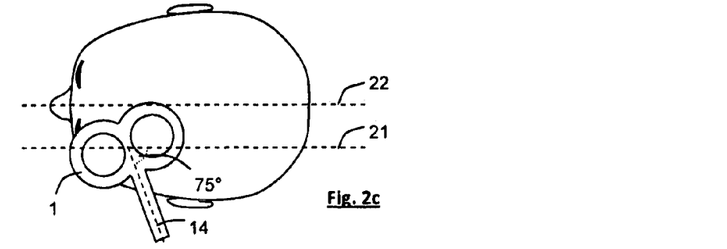
Figure 2D:
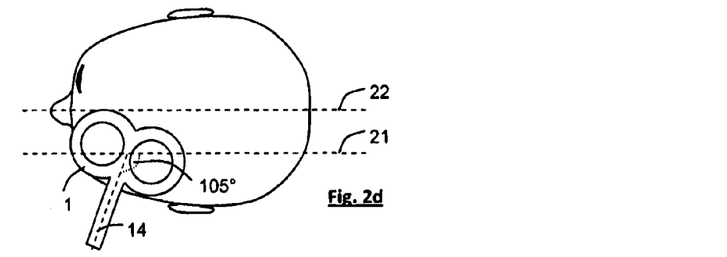
Figure 2E:
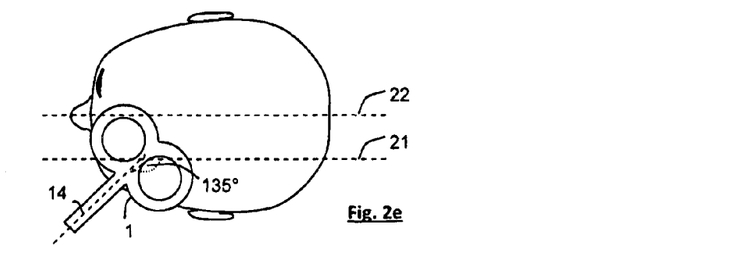

In embodiments of the present disclosure, TMS is administered using a 'figure-of-8' coil. An exemplary 'figure-of-8' coil 1 is shown in FIG. 1. The coil 1 has two identical loops (or 'wings') 11, 12 engaged together at a central region 13 of the coil. A central axis 14 of the coil 1 passes through the central region 13 and a centre 131 of the coil 1. The central axis 14 extends along the line of symmetry between the two loops 11, 12. A handle 15 is engaged with and extends from the central region 13 of the coil, and the elongation direction of the handle 15 is collinear with the central axis 14 in this embodiment.

With this coil configuration, electrical current can flow clockwise in one loop and counterclockwise in the other, resulting in unidirectional current flow at the centre of the coil, either towards or away from the handle. The current flow through the coil generates a magnetic field that can induce a flow of ionic current in a patient's cortex when the coil is held on or adjacent a region of the patient's scalp. Using the handle to change the orientation of the coil relative to the patient, e.g., relative to a sagittal or parasagittal plane of the patient, the direction of induced ionic current at the patient's cortex can be changed. Since neurons are preferentially activated (depolarized) by ionic current in certain directions, the degree of neuron activation will vary depending on the coil orientation.

The skilled person will appreciate, however, that the present disclosure is not limited to use of any particular type of coil, such as 'figure-of-8' coils. Any type of coil that is suitable for delivering TMS may be used.

With reference to FIGS. 2a to 2e, in an embodiment of the present disclosure, coil orientation is changed by rotating the coil 1 relative to a parasagittal plane 21. The coil orientation is described herein with reference to its angle relative to the parasagittal plane 21, and more particularly the angle between its central axis 14 and the parasagittal plane 21 (hereinafter the "coil angle"). Generally, a sagittal plane 22 is an imaginary longitudinal plane that divides a person into left and right halves (following the interhemispheric fissure), and any parasagittal plane 21 will lie parallel to the sagittal plane 22. The centre 131 ('hot spot') of the coil will tend to be located on a parasagittal plane, rather than the sagittal plane, when stimulation of cortical regions such as the prefrontal cortex (PFC) is carried out.

Figure 3:
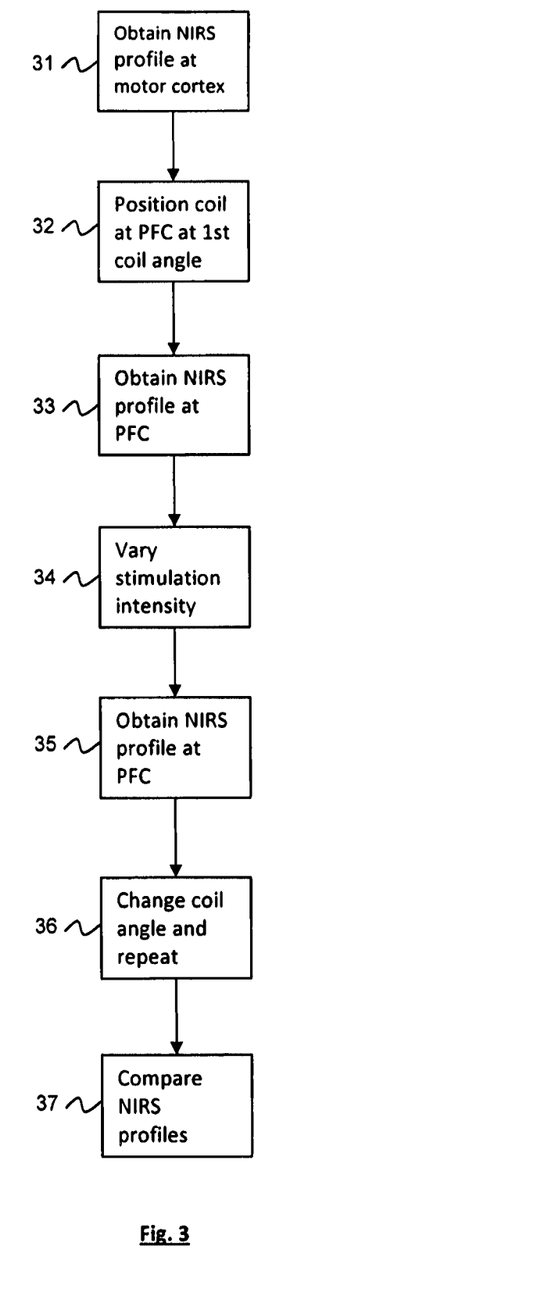
FIG. 3 is a flow chart showing steps taken in a method according to an embodiment of the present disclosure.

A transcranial magnetic stimulation method in accordance with an embodiment of the present disclosure is now described in more detail with reference to FIGS. 2a to 2e, and FIG. 3. Referring to FIG. 3, at a first stage 31, the coil 1 is positioned for TMS of the motor cortex of a patient and an electrical signal is delivered to the coil to generate magnetic field pulses for TMS. The stimulation intensity and optionally the coil orientation are varied while monitoring apparatus including an NIRS probe located adjacent the motor cortex is used to determine changes in DC, AC and phase of a signal collected from the NIRS probe, which changes are indicative of variation in HbO at the motor cortex during the TMS. EMG apparatus is used to determine when the changes correspond to a muscle response from the patient that is indicative of a resting motor threshold rMT having been reached. At this time, a NIRS response profile for the motor cortex at rMT is obtained 31.

At the next stage 32, the coil is located for TMS at the PFC of the patient. The coil is positioned at a first coil angle, e.g. a 15° angle (see FIG. 2a), and set at a first stimulation intensity. An NIRS response profile for the PFC at the first coil angle and stimulation intensity is obtained 33 using the monitoring apparatus described above. While maintaining the coil at that coil angle, the stimulation intensity is varied incrementally 34 and, for each stimulation intensity a further NIRS profile is obtained 35. The coil angle is then changed successively by e.g. 15° (see FIGS. 2b to 2e) and the process is repeated 36 such that an NIRS profile is obtained at the PFC for a plurality of different stimulation intensities at each different coil angle.

Either upon obtaining each NIRS profile for the PFC, or upon obtaining all NIRS profiles for the PFC, the NIRS profile(s) for the PFC are compared with the NIRS profile for the motor cortex. Optimal stimulation parameters (which may include threshold stimulation intensity and optimal coil orientation) for TMS at the PFC may be determined based on the comparison. For example, in one embodiment, to the extent that any NIRS profile for the PFC is considered to correspond to or is considered to be closest to the NIRS profile for the motor cortex, the coil angle and stimulation intensity that gave rise to that NIRS profile for the PFC can be deemed to have provided therapeutically relevant neuron activation at the PFC and therefore to be optimal stimulation parameters for TMS at the PFC, for the patient under test. For the PFC and motor cortex NIRS profiles to be considered to "correspond to" each other, the profiles need not necessarily be identical overall, but they may have consistent patterns or other features that are consistent and which are indicators of neuron activity. Where the PFC and motor cortex NIRS profiles are considered to be "closest to" each other, patterns or other features that indicate neuron activity need not necessarily be consistent, but increasing similarities in these features from one NIRS profile to the next may be recognisable, such as to allow one PFC NIRS profile to be determined as having a closer relationship to the motor cortex NIRS profile than another PFC NIRS profile, at least in relation to these features. Similar reasoning applies with respect to the use or analysis of combined NIRS and EEG profiles that are discussed further below.

It is conceivable that various combinations of coil angles and stimulation intensities may give rise to neuron activation at the PFC. Where a coil orientation is not the most optimised coil orientation, neuron activation at the PFC may still be realised if the stimulation intensity is sufficiently high. In view of this, it may be concluded that, in some circumstances, more optimal stimulation parameters for the PFC are those in which the coil orientation gives rise to the smallest stimulation intensity (the lowest stimulation threshold) needed to achieve neuron activation.

In alternative embodiments, substantially the same process as described above with respect to FIG. 3 can be carried out, but both NIRS analysis and EEG analysis may be employed to provide NIRS/EEG profiles for the motor cortex and PFC. This may enhance the amount of detail and accuracy provided by the profiles in order to indicate the degree and nature of neuron activity. In further alternative embodiments, instead of comparing NIRS or NIRS/EEG profiles for the PFC with an NIRS or NIRS/EEG profile for the motor cortex, they may be compared with a predetermined generic NIRS or NIRS/EEG profile for the PFC. In still further alternative embodiments, there may be no comparison of the determined NIRS or NIRS/EEG profiles with other profile types. Rather, a substantially isolated analysis of each of the determined NIRS or NIRS/EEG profiles may be undertaken in which, for example, feature extraction is carried out and/or an algorithm is be applied to profile data, such as to measure properties of the determined profiles, which properties may be used for comparison of the profiles.

Furthermore, in alternative embodiments, the differences by which the coil angle is varied, and the range over which the coil angles are varied, may be much smaller than discussed with respect to FIGS. 2a to 2e and FIG. 3. The differences in coil angles and range of coil angles discussed with respect to FIGS. 2a to 2e and FIG. 3 are relatively large in order to aid visual representation. While these differences and ranges of coil angles are intended to be encompassed by the present disclosure, in practice, coil angles may only be varied in some embodiments in steps of as little as 1°, for example, or lower, and/or coil angles may be varied in a range lying about a middle coil angle, e.g. 45°, that is as little as ±5°, for example, or lower. In some embodiments, an iterative process may be used to find an optimal coil angle, which process involves decreasing the differences between successive coil angles under test as the process gets closer to determining the optimal coil angle.

Still further, in alternative embodiments, NIRS may be replaced with other techniques suitable for monitoring changes in blood flow and/or blood oxygenation levels. An example alternative technique is functional magnetic resonance imaging (fMRI).

The method and apparatus described herein can be partially or entirely automated. A control unit may be used that is connected to an actuator configured to vary the coil angle, connected to the signal generator to vary the stimulation intensity, connected to the monitoring device (monitoring unit) to record NIRS, EEG and/or fMRI profiles, etc, and/or connected to an analysis unit to compare profiles, for example. At least the monitoring unit and analysis unit may be integrated with the control unit as part of a control device. In alternative embodiments, the coil may be hand-held by the operator and manipulated into the desired position and coil angle manually as required. The coil angle as well as the location of the centre of the coil relative to the cortical target region, amongst other things, can be represented on a display that is observable by the operator. Details may be displayed to the operator in 'real-time'. The coil angle and coil centre, etc., may be monitored using DC magnetic tracking or other types of spatial tracking device.

Figure 4:
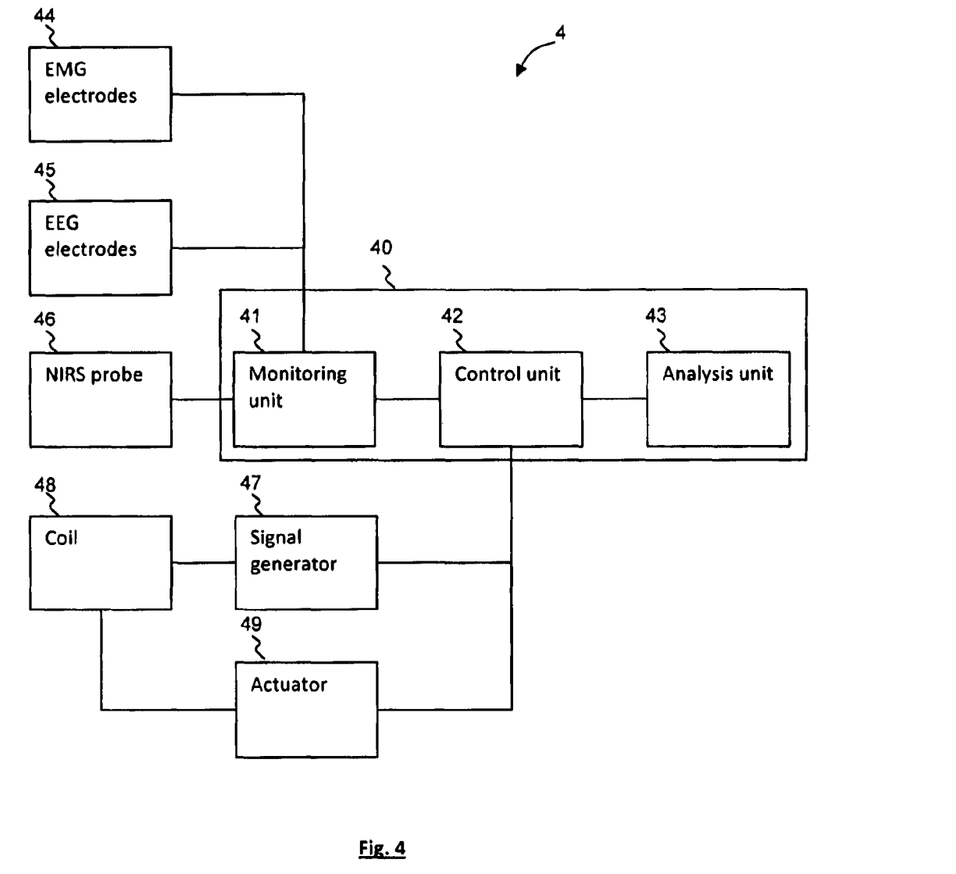
FIG. 4 shows a schematic view of apparatus according to an embodiment of the present disclosure.

A schematic view of an exemplary apparatus 4 that can be used in embodiments of the present disclosure is shown in FIG. 4. The apparatus comprises a control device 40 including a monitoring unit 41, a control unit 42 and an analysis unit 43. The monitoring unit 41 is configured to receive signals from EMG electrodes 44, EEG electrodes 45 and an NIRS probe 46 to determine rMT and NIRS/EEG profiles at the motor cortex and/or a non-motor target cortical region of a patient. The control unit 42 is connected to a signal generator 47 to vary stimulation intensity at a coil 48 and to an actuator 49 to vary the orientation of the coil 48. The rMT and NIRS/EEG profiles can be collected and analysed at the analysis unit 43 to determine TMS parameters in accordance with discussions above.

Generally, it will be recognised that any control device or processing unit (e.g. monitoring unit control unit or analysis unit, etc) disclosed herein may comprise a number of control or processing modules for controlling one or more components of the apparatus and may also include one or more storage elements, for storing TMS parameters and NIRS or NIRS/EEG profiles, etc. The modules and storage elements can be implemented using one or more processing devices and one or more data storage units, which modules and/or storage devices may be at one location or distributed across multiple locations and interconnected by one or more communication links.

The processing modules can be implemented by a computer program or program code comprising program instructions. The computer program instructions can include source code, object code, machine code or any other stored data that is operable to cause the processor to perform the steps described. The computer program can be written in any form of programming language, including compiled or interpreted languages and can be deployed in any form, including as a stand-alone program or as a module, component, subroutine or other unit suitable for use in a computing environment. The data storage device(s) may include suitable computer readable media such as volatile (e.g. RAM) and/or non-volatile (e.g. ROM, disk) memory or otherwise.

EXAMPLES

Four example studies were conducted to verify that changes in HbO levels were observable for different coil orientations (current directions) for TMS at the PFC using NIRS. Study 1 compared the effects on HbO levels of single pulse TMS delivered at two different coil angles, 45 degrees and 135 degrees. Study 2 compared the effects on HbO levels of repetitive pulse TMS delivered at two different coil angles, 45 degrees and 225 degrees. Study 3 examined the effects of single pulse TMS (at 120% resting motor threshold) delivered at five different angles, 15, 30, 45, 60, and 75 degrees, using both NIRS and EEG. Study 4 examined the effects of single pulse TMS (at an angle of 45 degrees) delivered at five different intensities, 70, 80, 90, 100, 110, and 120% of resting motor threshold, using both NIRS and EEG. Study 1 aimed to show that TMS delivered at 135 degree coil angles results in reduced cortical depolarization, and consequently a reduced change in HbO would be observed. Study 2 aimed to show that TMS delivered at 225 degree coil angles results in reduced cortical depolarization, and consequently a reduced change in HbO would be observed. Study 3 aimed to show that there is a coil orientation specific to each individual that produces a large negative deflection in HbO and cortical potential. Study 4 aimed to show that the level of cortical activation increases with increasing intensity and that the pattern of HbO is differentiated (with increasing intensity) between low cortical activation, cortical activation sufficient to evoke a normal hemodynamic response to oxygen demands (net positive change in HbO), and cortical activation where oxygen requirements are greater than supply resulting in a net decrease in HbO.

Example Study 1—Method

Data was collected for 12 subjects (5 females, age 25-47 years).

Initially, resting motor threshold (rMT) was determined for the subject by recording electromyographic (EMG) activity from Ag/AgCl surface electrodes placed over the first dorsal interosseus (FDI) muscle in a belly-tendon montage. The signal was amplified (1000×), filtered (20-2000 Hz), and sampled at 5 kHz. Resting motor threshold (rMT) was defined as the minimal TMS intensity needed to evoke a motor evoked potential (MEP) in the right FDI that was larger than 50 µV in three of five consecutive trials. TMS was applied using a 'figure-of-8' coil over the left hemisphere at a 45° angle from a parasagittal plane by a Magstim 200™ (Magstim, Whitland, Dyfed, UK).

During the experimental conditions, the TMS was applied over the PFC, between F3 and AF3 in the 10-20 system, just posterior to the hairline and the location of an NIRS probe. An additional NIRS probe was located on the contralateral hemisphere to allow comparison between the left and right hemispheres (ipsilateral and contralateral PFC) during TMS. A total of 30 pulses at two different coil orientations (45° or 135° angle from the parasagittal plane) were delivered at 130% of rMT at an inter-pulse interval of 25 seconds. The condition order was counterbalanced across subjects. The two conditions had extremely similar stimulatory properties from the subject's perspective, namely an identical auditory click stimulus and a very similar scalp sensation, since real TMS at the same intensity is being delivered. Given that the auditory and somatosensory stimulation to the participant is the same, the effect of current/coil orientation could be more effectively isolated.

For NIRS analysis, an Oximeter Model 96108™ (OxiTS; ISS Inc, Champaign, Ill., USA) was used to collect DC, AC, and phase data for two wavelengths (687 nm & 830 nm) sampled at 50 Hz. The Differential Pathlength Factor (DPF) (Fantini, S. et al. *Non-invasive optical monitoring of the newborn piglet brain using continuous-wave and Frequency-domain spectroscopy. Physics in medicine and biology* 44, 1543-1563 (1999)) and change in absorption were calculated from the AC and phase and changes in HbO were then calculated with the extinction coefficients corresponding to the selected wavelengths. Quantifying these changes assumed a homogenous scattering medium, an assumption that may be nullified by the non-homogenous layering of head tissues, hence they are expressed in arbitrary units (a.u.) (Toronov, V. et al. *Investigation of human brain hemodynamics by simultaneous near-infrared spectroscopy and functional magnetic resonance imaging. Medical physics* 28, 521-527 (2001)). The signal was filtered (0.005-0.5 Hz), trials were epoched around the TMS (those that were contaminated by movement artifact were removed), baseline corrected, and averaged. The mean blood oxygenation was measured 5 seconds prior to stimulation (pre-stim) and at a 5 second interval after stimulation (post-stim) centered around the period of maximum change (10 seconds post-stim). The TMS evoked hemodynamic response for each coil orientation (45° and 135°) and each hemisphere (left and right PFC) was analyzed by 2×2 factor ANOVA. Multiple comparisons were controlled for by Holm-Bonferroni correction. Pearson correlations between the left and right hemispheres were also evaluated.

Example Study 1—Results

Figure 5A:
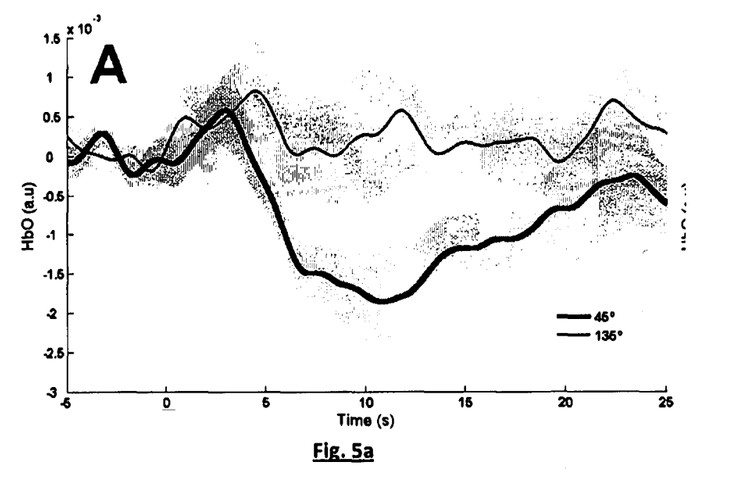
FIGS. 5a and 5b show graphs of average change in oxygenated hemoglobin (HbO) across subjects following single pulse TMS with coil angles of 45° and 135°, measured at the ipsilateral (A) and contralateral PFC (B) respectively, wherein shaded areas represent standard error.
Figure 5B:
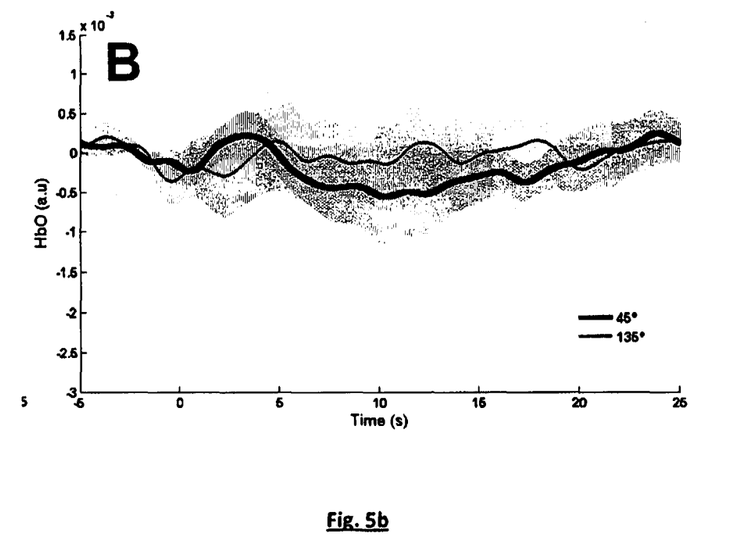

The 2×2 factor ANOVA revealed a significant main effect for orientation, $F(1, 11)=5.8$, $p<0.05$ but not for hemisphere ($F(1, 11)=2.4$, $p=0.15$). There was a significant interaction between orientation and hemisphere, $F(1, 11)=5.3$, $p<0.05$ (FIGS. 5a and 5b). This interaction was driven by a reduction in HbO in the 45° condition that was not observed at 135° in the ipsilateral (left) PFC ($p<0.01$) and of lower magnitude in the contralateral PFC ($p<0.05$). Mean values (±standard error) are as follows: Left PFC/45°: −10.1±3.5; Left PFC/135°: 1.6±4.4; Right PFC/45°: −2.9±3.2; Right PFC/135°: −0.3±3.3.

Example Study 2—Method

Data was collected for 8 subjects (4 females, age 22-42 years). A similar procedure to determine rMT to that described with respect to Study 1 was followed, but though application of repetitive pulse TMS by a MagVenture R30™ with a cooled coil. Furthermore, a similar procedure to apply TMS over the PFC to that described with respect to Study 1 was also followed. However, biphasic TMS was applied at 120% of RMT and a total of 30 trains of 1 Hz rTMS were administered with a 20 second train length and a 40 second inter-train interval at two orientations, 45° and 225°.

For NIRS analysis, a similar procedure to that described with respect to Study 1 was followed, although the mean blood oxygenation was measured over a 10 second interval (post-stimulation) centered around the period of maximum change (immediately following the train, 20 seconds post-stimulation).

Example Study 2—Results

Figure 6A:
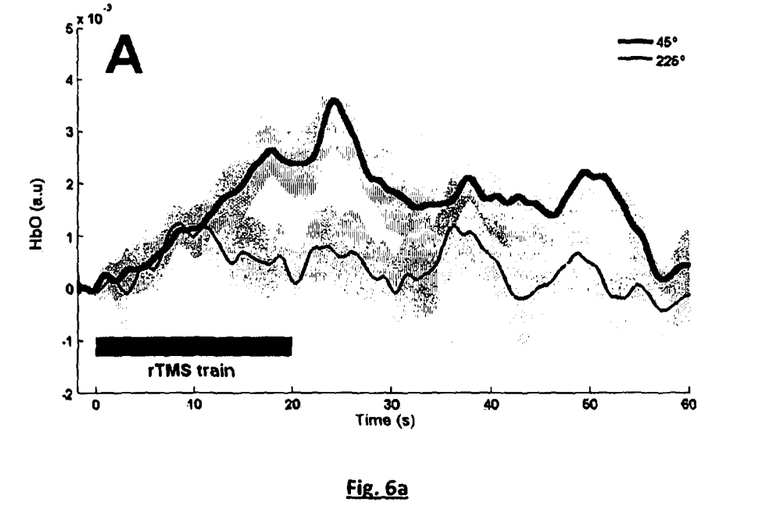
FIGS. 6a and 6b show graphs of average change in oxygenated hemoglobin (HbO) across subjects following 20 s 1 Hz rTMS trains with coil angles of 45° and 225°, measured at the ipsilateral (A) and contralateral PFC (B), respectively. Shaded areas represent standard error.
Figure 6B:
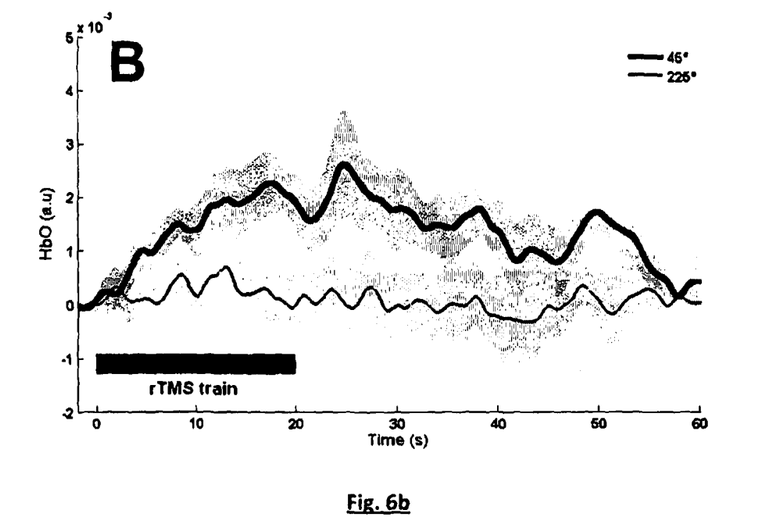

There was a significant main effect of orientation, $F(1,7)=11.5$, $p<0.02$ and a significant increase in HbO bilaterally when stimulation was provided at 45° (particularly ipsilaterally) with only a small change in HbO at 225° (FIGS. 6a and 6b). However, there was no main effect of hemisphere or interaction observed. Mean values (±standard error) are as follows: Left PFC/45°: 15.8±3.7; Left PFC/225°: 3.3±3.6; Right PFC/45°: −12.1±3.8; Right PFC/225°: 0.9±5.2.

Example Study 3—Method

Data was collected for 2 subjects (1 female, age 24 & 35 years). A similar procedure to that described in studies 1 and 2 was followed to record NIRS, but at 15°, 30°, 45°, 60° and 75° coil orientations. For each subject EEG recording was measured at F3 on the International 10-20 system referenced to electrodes located at the mastoids using a SynAmps2™ (Compumedics, Charlotte N.C., USA) system. The signal was filtered (0.1-30 Hz), trials were epoched around the TMS (those that were contaminated by artifact were removed), baseline corrected, and averaged.

Example Study 3—Results

Figure 7:
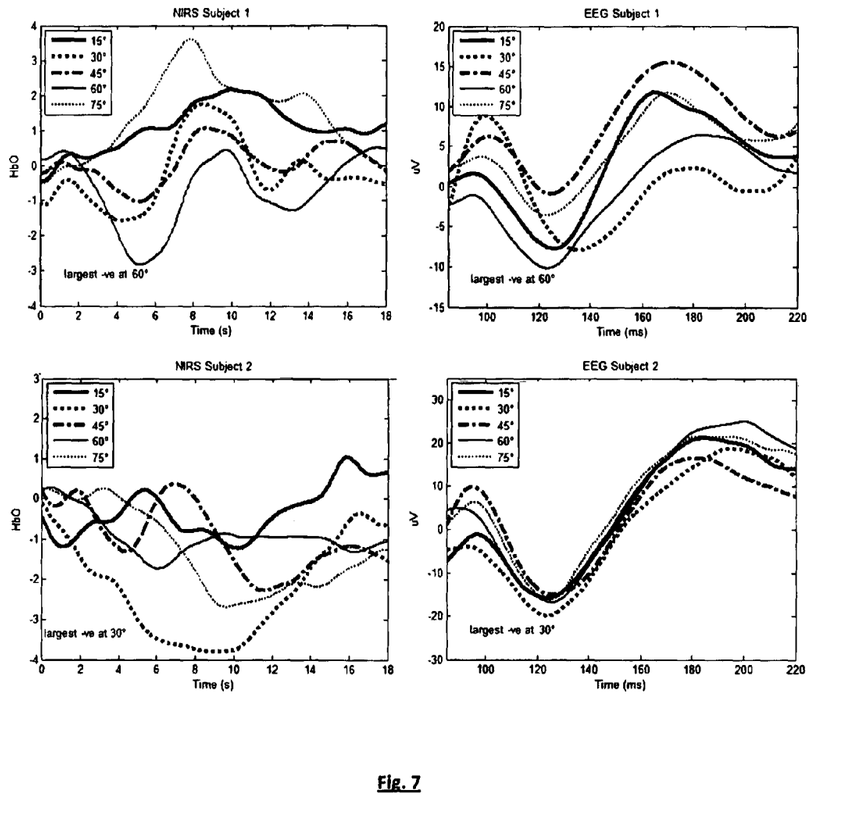
FIG. 7 shows graphs of average change in oxygenated hemoglobin (HbO) and cortical evoked potential in two subjects following single pulse TMS with coil angles of 15, 30, 45, 60, and 75°.

Both the NIRS and EEG measurements indicated a maximal activation for subject 1 with a 60 degree coil orientation and a maximal activation for subject 2 with a 30 degree coil orientation (FIG. 7). This demonstrated that, while approximately 45 degrees might generally be an optimal coil orientation, if the coil orientation is to be fixed across a plurality of subjects, the optimal coil orientation can vary from one subject to another.

Example Study 4—Method

Figure 8:
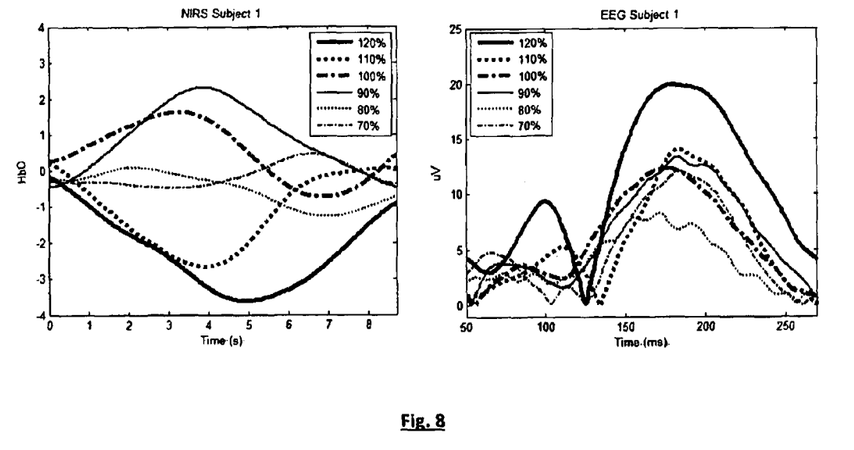
FIG. 8 shows graphs of average change in oxygenated hemoglobin (HbO) and cortical evoked potential following single pulse TMS with TMS intensity of 70, 80, 90, 100, 110, and 120% of resting motor threshold.

Data was collected for 1 subject (female, age 24). A similar procedure to that described in study 3 was followed to record NIRS and EEG, but with a coil angle of 45° and TMS intensities of 70, 80, 90, 100, 110, and 120% of resting motor threshold Example Study 4—Results Both the NIRS and EEG measurements indicated a maximal activation at 120% (FIG. 8). The EEG measurement demonstrated an approximately graded increase in area under the curve with increasing intensity. The NIRS measurement exhibited minimal HbO change following low intensities (70 and 80%), a normal hemodynamic response following intensities close to motor threshold (90% and 100%), and depleted oxygen following potentially 'unnatural' brain activation following high intensities (110% & 120%). This demonstrated that the threshold for a normal hemodynamic response and the threshold for a depleted oxygen response varies between subjects.

Examples—Discussion

With reference to FIGS. 5a and 5b, the study found that there was a significantly greater drop in HbO at coil angles of 45° in the targeted ipsilateral hemisphere compared to coil angles of 135°. With reference to FIGS. 6a and 6b, the study found that there was a significantly greater change in HbO at coil angles of 45° bilaterally compared to coil angles of 225°. With reference to FIG. 7, the study found that the optimal coil orientation on an individual basis can vary by small degrees away from 45 degrees. With reference to FIG. 8, the study found that the EEG response and HbO response to varying intensity can indicate the threshold at which different aspects of cortical activation and hemodynamic response can be evoked. Overall the studies indicate that neural activity evoked by TMS at PFC is dependent upon current direction (and thus coil orientation) and the intensity of TMS, and that this can be effectively analysed by monitoring changes in blood flow and/or blood oxygenation at the PFC, e.g., using a combination of EEG and NIRS.

These findings have implications for the delivery of TMS outside of the motor cortex, particularly in the case of clinical rTMS. Examples of this include the treatment of major depressive disorder, in which rTMS is often delivered to DLPFC, and the treatment of auditory hallucinations in schizophrenia which targets temporoparietal regions. The studies underscore the importance of current direction in evoking neural activity by TMS, and highlight the clinical need for an individual measurement of TMS efficacy at regions outside of motor cortex. The ability to calibrate rTMS dose based on a localized neural response is likely to improve clinical outcomes.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of optimising transcranial magnetic stimulation comprising:
    positioning a coil having a coil centre at a location relative to a target cortical region of a patient, wherein the target cortical region is a region outside of the motor cortex;
    applying an electrical signal to the coil to generate one or more magnetic field pulses for transcranial magnetic stimulation of the target cortical region of the patient, wherein the transcranial magnetic stimulation has stimulation parameters including orientation of the coil relative to the patient and intensity of the magnetic stimulation;
    while maintaining the coil centre at the location, varying at least the orientation of the coil relative to the patient;
    at different orientations of the coil relative to the patient, monitoring neuron activation at the target cortical region using near infra-red spectroscopy (NIRS); and
    based on information obtained during the monitoring, determining one or more optimal coil orientations for the transcranial magnetic stimulation.

2. The method of claim 1 comprising, at one or more of the different coil orientations, varying the magnetic stimulation intensity, and, at different coil orientations and magnetic stimulation intensities, monitoring neuron activation at the target cortical region using near infra-red spectroscopy (NIRS).

3. The method of claim 2, wherein the magnetic stimulation intensity is varied by varying one or more parameters of the electrical signal including current level, pulse frequency and/or pulse width.

4. The method of claim 1, wherein the neuron activation is quantified by monitoring changes in DC, AC and/or phase of a collected NIRS signal.

5. The method of claim 1, wherein the target cortical region is a pre-frontal cortex.

6. The method of claim 1, comprising:
    performing transcranial magnetic stimulation of the motor cortex of the patient;
    monitoring the motor cortex, wherein the monitoring of the motor cortex includes monitoring neuron activation at the motor cortex using near infra-red spectroscopy (NIRS) to obtain an NIRS profile at the motor cortex at which motor threshold of the patient is achieved;
    performing the transcranial magnetic stimulation of the target cortical region;
    varying one or more of the stimulation parameters including at least the coil orientation;
    monitoring the target cortical region, wherein the monitoring of the target cortical region includes monitoring neuron activation at the target cortical region using near infra-red spectroscopy (NIRS) to obtain NIRS profiles at the target cortical region for different stimulation parameters; and
    comparing the NIRS profiles obtained at the target cortical region with the NIRS profile obtained at the motor cortex to determine one or more optimal stimulation parameters for transcranial magnetic stimulation of the target cortical region.

7. The method of claim 6, wherein, to determine the optimal stimulation parameters, the stimulation parameters which provide an NIRS profile at the target cortical region that corresponds to or is closest to the NIRS profile at the motor cortex are determined.

8. The method of claim 6, comprising:
    in the step of monitoring the motor cortex, monitoring electric fields at the motor cortex using EEG to obtain, in addition to the NIRS profile, an EEG profile at the motor cortex at which motor threshold of the patient is achieved;

in the step of monitoring the target cortical region, monitoring electric fields at the target cortical region using EEG to obtain, in addition to the NIRS profiles, EEG profiles at the target cortical region for the different stimulation parameters; and comparing the NIRS and EEG profiles obtained at the target cortical region with the NIRS and EEG profile obtained at the motor cortex to determine one or more optimal stimulation parameters for transcranial magnetic stimulation of the target cortical region.

9. The method of claim 8, wherein, to determine the optimal stimulation parameters, the stimulation parameters which provide an NIRS and EEG profile at the target cortical region that corresponds to or is closest to the NIRS and EEG profile at the motor cortex are determined.

10. The method of claim 1, comprising monitoring electric fields at the target cortical region using EEG for different stimulation parameters.

* * * * *